United States Patent [19]

Isenberg et al.

[11] Patent Number: 5,232,692

[45] Date of Patent: Aug. 3, 1993

[54] POVIDONE-IODINE NEONATAL OPHTHALMIC ANTIMICROBIAL PROPHYLACTIC AGENT

[75] Inventors: Sherwin J. Isenberg; Leonard Apt, both of Los Angeles, Calif.

[73] Assignee: Research and Education Institute, Inc., Torrance, Calif.

[21] Appl. No.: 344,894

[22] Filed: Apr. 28, 1989

[51] Int. Cl.⁵ .................... A61K 31/74; A61K 33/36
[52] U.S. Cl. .................................. 424/78.04; 424/667
[58] Field of Search ........................... 424/667, 78.04

[56] References Cited

U.S. PATENT DOCUMENTS 4,401,651  8/1983  Knutson ............................. 514/53

OTHER PUBLICATIONS

Chem Abst. 78: 106019p (1973), White et al.
Chem Abst. 105: 17912h (1986), Roberts et al.

*Primary Examiner*—Zohreh A. Fay
*Attorney, Agent, or Firm*—Drucker & Sommers

[57] ABSTRACT

A composition for neonatal ophthalmic prophylactic and a method of applying the composition. The composition comprises an aqueous solution of povidone-iodine having a concentration ranging from 5 percent to 0.1 percent. The composition of this invention prevents conjunctivitis caused by gonococus and other bacteria including chlamydia, as well as viruses and fungi.

10 Claims, No Drawings

POVIDONE-IODINE NEONATAL OPHTHALMIC ANTIMICROBIAL PROPHYLACTIC AGENT

BACKGROUND OF THE INVENTION

This invention relates to uses of povidone-iodine, particularly uses of povidone-iodine as ophthalmic preparations.

U.S. Pat. No. 2,706,701 issued to Beller teaches a polyvinylpyrrolidone-iodine (povidone-iodine) composition that has proven to be an effective antimicrobial topical preparation. Topical uses include sterilization of skin, either on a proposed incision site, or the hands of the surgical team.

The primary purpose of povidone-iodine is its use as an antiseptic preparation. U.S. Pat. No. 4,113,857 issued to Shetty teaches various uses of povidone-iodine. These uses include mouthwashes, handwashes, ointments, shampoos, douches, scrubs, and gargles.

In the United States, newborn babies are universally given topical prophylactic antimicrobial ophthalmic treatment. This procedure is used to prevent various types of infectious conjunctivitis, especially those caused by the gonococcus (*Neisseria gonnorrhoeae*) and chlamydia (*Chlamydia trachomatis*) microorganisms.

The conventional topical drug for neonatal ophthalmic antimicrobial prophylaxis has been silver nitrate. However, silver nitrate is somewhat irritating and can cause chemical conjunctivitis. This chemically-induced cojunctivitis can be differentiated from bacterial conjunctivitis only by culturing the conjunctiva of the affected individual to exclude the presence of bacteria. Furthermore, although silver nitrate has excellent activity against the gonococcus, it has poor activity against the chlamydia microorganism.

In response to the problem of chemical conjunctivitis, and the fact that silver nitrate is ineffective against *Chlamydia trachomatis*—now the most common cause of neonatal conjunctivitis—physicians in recent years have begun to use antibiotic ointments or eyedrops, namely, tetracycline or erythromycin, for neonatal ophthalmic prophylaxis. Unfortunately, reports indicate that these antibiotics are not always effective in preventing gonococcal or chlamydial conjunctivitis. These failures have prompted some hospitals serving populations at high risk of gonorrheal infections to resume using silver nitrate prophylaxis. The rationale is that chlamydial conjunctivitis rarely causes blindness in newborns, whereas gonorrhea can cause blindness within twenty-four hours.

It has also been established that neonates have large populations of anaerobic bacteria on their eyes. These bacteria may be the cause of some cases of neonatal conjunctivitis of supposed unknown origin some cultures are for bacteria are not routinely taken. Therefore, an ideal antimicrobial prophylactic agent should also have anti-anaerobic bacterial action.

As an added complication, new venereal diseases seem to be appearing with increasing frequency. As the neonate travels through the birth canal the infant can be exposed to the veneral disease infecting the mother. Any one of these diseases might cause neonatal ophthalmic complications if left untreated. Diseases caused by viruses such as herpes simplex or acquired immunodeficiency syndrome (AIDS), and fungal infections such as those caused by Candida, are not affected by silver nitrate or antibiotics. In the case of AIDS, about 50 percent of infants of mothers who are immunopositive for HIV, (the AIDS virus) are born infected. Since the eye is known to be a portal of entry of organisms into the body, the prompt use of an ophthalmic prophylactic agent effective against HIV may prevent infection that may occur from exposure to maternal blood or secretions during birth. Therefore, any proposed new neonatal ophthalmic prophylactic drug must have a wide range of antimicrobial activity.

It would be highly advantageous to have a chemical prophylactic agent that is relatively nonirritating and that has a broad antimicrobial spectrum, preferably including aerobic and anaerobic bacteria, richettsia, viruses, and fungi. Povidone-iodine is known to have activity against these microoganisms including HIV.

One known ophthalmic use for povidone-iodine is in preparing the eye for surgery. However, a presurgical preparation needs to have substantially different properties than a neonatal antimicrobial prophylatic preparation. For example, different bacteria are found in the eyes of newborns, than in the eyes of older children and adults. Because of their recent passage through the birth canal, newborns have ophthalmic bacterial flora more closely resembling an adult female's genital bacterial flora. In addition, the eye of a newborn may be more sensitive or delicate and may require different concentrations of povidone-iodine than that suitable for a preoperative preparation for an adult.

SUMMARY OF THE INVENTION

This invention provides a neonatal ophthalmic antimicrobial phophylactic agent, and a method of applying the prophylactic agent. The prophylactic agent comprises an aqueous solution of povidone-iodine having a concentration ranging from 5 percent to 0.1 percent (0.5% to 0.01% available iodine). The prophylactic agent prevents conjunctivitis caused by aerobic and anaerobic bacteria, richettsia, viruses and fungi. In particular, conjunctivitis caused by both gonococus and chlamydia micro-organisms are prevented.

An aspect of this invention is a neonatal ophthalmic prophylactic agent comprising:

an aqueous solution of povidone-iodine in the range of between 5 percent and 0.1 percent (0.5% to 0.01% available iodine).

Another aspect of this invention is a method for administering neonatal ophthalmic antimicrobial prophylactic comprising:

contacting the eyes of a neonate with an aqueous solution of povidone-iodine having a concentration of between 5 percent and 0.1 percent.

Povidone-iodine provides a prophylaxis that is nonirritating and has a broad spectrum of antimicrobial action. Furthermore, providone-iodine is an antiseptic. Therefore the possibility of a micro-organism developing resistance to povidone-iodine is very much lower than for antibiotics.

DETAILED DESCRIPTION

Definitions

"Povidone" is the commonly used name for polymeric 1-vinyl-2-pyrrolidone.

Concentrations of iodine are expressed herein as concentrations of total iodine. Iodine concentration can be expressed as total iodine, which includes iodine that is too tightly complexed with povidone to be useful, available iodine, which is the iodine that is potentially available for antiseptic use, and free iodine, which is that iodine that provides the antiseptic qualities to the preparation. A 10 percent povidone-iodine solution contains about 1 percent available iodine and less then 1 ppm free iodine.

"Neonate" as used herein refers to infants less than thirty days old and preferably less that one day old.

"Solution" as used herein a liquid solution, gel, a salve, an ointment or other substantially aqueous preparation that can be placed in the neonate's eye. The precise nature of the physical properties and chemical composition of the solution are unimportant as long as the solution is largely aqueous, it is nonirritating to the neonates eye and it has from 5.0 to 0.1 percent povidone-iodine. The solution may be entirely aqueous, or it may include an emulsifying agent, for example, petrolatum.

Utility

In the practice of this invention, one or more drops of aqueous povidone-iodine ophthalmic antimicrobial solution are placed in a neonate's eyes within six hours of birth, preferably, within one hour after birth. The aqueous povidone-iodine solution will have a concentration of between 5 percent and 0.1 percent. Preferable concentrations of povidone-iodine solution are between 1.0 percent and 0.5 percent, more preferable concentrations are in the range of about 1.0 percent to 2.0 percent, and most preferable concentrations are in the range of 2.0 percent to 5.0 percent. Various pharmaceutical formulations may be used—liquids, salves, gels, emulsions, and the like are all acceptable. Pharmaceutically acceptable excipients and adjuvants may be added to the preparation as well.

One composition suitable for use in this invention can be made by diluting a given volume of commercially available 10 percent povidone-iodine solution with enough distilled water, physiological saline, or a balanced salt solution to create the desired concentration. An equivalent volume of water or salt solution gives a five percent solution, ten times more water or salt solution gives a 0.5 percent solution. The dilution is made just prior to use in the eye. A diluant with stabilizing elements may be used to increase the reasonable shelf-life of the product.

When an ointment or gel is preferred, the liquid solution can be thickened by addition of gelatin or similar hydrophillic agent, as a liquid solution may be emulsified with petrolatum or similar petroleum based thickener. If an ointment is formulated the total povidone-iodine of the formulation will be in the range of 5.0 percent to 0.1 percent.

A drop or several drops are placed in the neonates eyes, preferably within two hours after birth. Care is taken to assure that the formulation is not irrigated out of the neonates eye. The proliferation of any bacteria, fungi, or viruses and consequent infection of the neonates eye is thereby prevented.

The effect on the bacterial flora of neonatal eyes can be tested by comparing the progress of a series of neonates who have had one eye treated with providone-iodine and the other treated with a conventional agent, either silver nitrate or an antibiotic, for example, tetracycline or erythromycin. Bacterial swabs are taken before, immediately after, and several days after administration of the providone-iodine formulation. The eye given the providone-iodine solution will consistently have fewer aerobic and anaerobic bacteria, viruses and fungi than the conventionally treated eye.

It has been proven that anaerobic bacteria are present on neonatal eyes. These bacteria can cause conjunctivitis and are a leading contender for the major cause of conjunctivitis of unknown etiology. Administration of povidone-iodine to the eye promptly after birth will prevent conjunctivitis caused by anaerobic bacteria.

We claim:

1. A method for neonatal ophthalmic prophylaxis comprising:
    contacting the eyes of a human neonate with an aqueous solution of consisting essentially of povidone-iodine having a concentration between 5 percent and 0.1 percent thereby preventing infection with *Neisseria gonorrhea* or *Chlamydia trachomatis*.

2. The method of claim 1, wherein the total concentration is between 0.1 percent and 2.0 percent.

3. The method of claim 1, wherein the total concentration is between 0.75 percent and 1.5 percent.

4. The method of claim 1, including a pharmaceutically acceptable excipient.

5. The method of claim 1, wherein said aqueous solution is substantially liquid.

6. The method of claim 1 including the step of placing between 1 to 6 drops of a liquid povidone-iodine solution in each neonatal eye.

7. The method of claim 1 including the step of placing between one and two drops of povidone-iodine solution in each neonatal eye.

8. The method of claim 1 including the step of placing an effective amount of povidone-iodine containing gel in each neonatal eye.

9. The method of claim 1 including the step of placing an effective amount of povidone-iodine containing ointment in each neonatal eye.

10. A method for neonatal prophylaxis comprising:
    contacting the eyes of a human neonate with a non-irritating aqueous solution consisting essentially of povidone:iodine having a concentration in range of between 2.5 percent and 0.1 prevent thereby preventing infection with *Neisseria gonorrhoea* or *Chlamydia trachomatis*.

* * * * *